United States Patent
Felici et al.

(10) Patent No.: US 11,185,713 B2
(45) Date of Patent: Nov. 30, 2021

(54) IORT DEVICE FOR RADIOTHERAPY TREATMENT OF CANCER PATIENTS

(71) Applicant: S.I.T.-SORDINA IORT TECHNOLOGIES S.P.A., Vicenza (IT)

(72) Inventors: Giuseppe Felici, Vicenza (IT); Massimo Di Francesco, Anzio (IT)

(73) Assignee: S.I.T.-SORDINA IORT TECHNOLOGIES S.P.A., Vicenza (IT)

(*) Notice: Subject to any disclaimer, the term of this patent is extended or adjusted under 35 U.S.C. 154(b) by 8 days.

(21) Appl. No.: 16/959,388

(22) PCT Filed: Jan. 14, 2019

(86) PCT No.: PCT/IT2019/050003
§ 371 (c)(1),
(2) Date: Jun. 30, 2020

(87) PCT Pub. No.: WO2019/142217
PCT Pub. Date: Jul. 25, 2019

(65) Prior Publication Data
US 2021/0060356 A1  Mar. 4, 2021

(30) Foreign Application Priority Data
Jan. 18, 2018  (IT) .................. 102018000001312

(51) Int. Cl.
*A61N 5/10*  (2006.01)
*G21K 1/10*  (2006.01)

(52) U.S. Cl.
CPC ............ *A61N 5/10* (2013.01); *G21K 1/10* (2013.01); *A61N 2005/1089* (2013.01); *A61N 2005/1094* (2013.01)

(58) Field of Classification Search
None
See application file for complete search history.

(56) References Cited

U.S. PATENT DOCUMENTS 4,359,642 A * 11/1982 Heinz ............... G21K 1/02
                                         250/505.1
10,525,285 B1 * 1/2020 Friedman ......... A61N 5/1067
(Continued)

FOREIGN PATENT DOCUMENTS

WO  2014125516 A1  8/2014
WO  2014195986 A1  12/2014

OTHER PUBLICATIONS

Search Report of the prior Italian patent application by the Italian Patent Office dated Oct. 24, 2018.

*Primary Examiner* — Hoon K Song
(74) *Attorney, Agent, or Firm* — Platinum Intellectual Property LLP

(57) ABSTRACT

An IORT device (10) for radiotherapy treatment of cancer patients, comprising a source of particles, an accelerating device (11), which sends a beam of particles (12) on a target (14) through an applicator (15), a scattering filter (16), which allows the distance between the source of particles and the target (14) to be kept within a range compatible with the use of IORT devices (10) in standard operating rooms, and an optical system for collimating the beam of particles (12), which is placed between the scattering filter (16) and the applicator (15); specifically, the optical collimating system of the beam of particles comprises a primary screen (17), configured to shield the radiation produced by the scattering filter (16), a secondary screen (18), configured to shield the photons produced on the primary screen (17), and a collimating apparatus (19), which provides for housing the monitor chambers (20).

8 Claims, 2 Drawing Sheets

(56) References Cited

U.S. PATENT DOCUMENTS

| | | | | |
|---|---|---|---|---|
| 2011/0017920 A1* | 1/2011 | Goer | ............... | A61N 5/10 |
| | | | | 250/396 R |
| 2011/0224477 A1* | 9/2011 | Issels | ............... | A61N 1/403 |
| | | | | 600/2 |
| 2012/0189106 A1* | 7/2012 | Verhaar | ............... | A61N 5/10 |
| | | | | 378/198 |
| 2019/0054318 A1* | 2/2019 | Goer | ............... | A61N 5/1067 |

* cited by examiner

IORT DEVICE FOR RADIOTHERAPY TREATMENT OF CANCER PATIENTS

RELATED APPLICATIONS

This application is a United States National Stage Application filed under 35 U.S.C 371 of PCT Patent Application Serial No. PCT/IT2019/050003, filed Jan. 14, 2019, which claims Italian Patent Application Serial No. IT 102018000001312, filed Jan. 18, 2018, the disclosure of all of which are hereby incorporated by reference in their entirety.

This invention relates, in general, to an IORT device for radiotherapy treatment of cancer patients.

The most feared illnesses of modern times undoubtedly include tumours, due to the high mortality rates of some types of tumours and the difficulty treating them.

A tumour or, less commonly, neoplasia or cancer, if malign, consists of a class of illnesses characterized by uncontrolled reproduction of some cells of the body, which stop responding to cellular control physiological mechanisms following damage to their genetic makeup.

In order to become tumorous, a cell has to go haywire, that is to say, an error must occur in the system that controls its reproduction; in fact, all cancerous and pre-cancerous cells have very extensive alterations in their chromosomal composition: the number of chromosomes present in their nucleus is changed and the chromosomes themselves are damaged, multiple or missing.

The chromosomal change of tumorous cells is so serious and extensive that it provides evidence that in all cases of tumours all of the cancerous cells are descendants of a single mutated mother cell.

This random genetic chaos explains the extreme variability in terms of appearance, effects, symptoms and prognosis of the many forms of cancer still known.

Despite having a single general originating mechanism, tumours can manifest a very wide range of developments and symptomologies. However, something that is constant for all of them is an increase in the number of cancerous cells, due to the higher speed of cell reproduction, meaning that a higher number of tumorous cells multiply and a lower number of them die, whilst those which survive keep multiplying.

The growth of a tumour usually follows a geometric law: at the start it is very slow, but it accelerates as the tumour mass increases. The critical size of a tumour is approximately one cubic centimetre: once it has reached that size, the tumour begins to grow very rapidly and to cause the initial symptoms and it becomes detectable with medical examinations and tests.

However, often initial symptoms are ignored or underestimated.

The great speed of reproduction of cancerous cells forms the basis of the need and urgency to treat it as soon and as effectively as possible, that is to say, eliminating with the greatest possible degree of certainty all "affected" cells, since, as already indicated, the tumour may evolve, and therefore come back, even from a single mutated cell.

The most widely known treatment for cancer is surgery. With this, if possible, attempts are made to remove what is defined as the tumorous mass, that is to say, the set of mutated cells, and what surrounds them. That treatment method is not always usable or, when used, is not always sufficient to guarantee the desired result. In fact, it is impossible to know if the tumour has also affected the surrounding or adjacent cells, which appear healthy; moreover it is possible that the surgery itself results in dissemination of tumorous cells.

For those reasons, in combination with or as an alternative to surgery, chemotherapy and radiotherapy are also used.

Radiotherapy consists of using ionizing radiation to irradiate neoplastic tissue and/or tissue adjacent to the neoplasia.

Chemotherapy exploits the specific sensitivity of the individual tumours to certain substances, and, for each patient, a customized mixture of multiple drugs is designed. This mixture almost always contains one or more cell division inhibitors, to prevent cell proliferation. However, these drugs cause some serious and undesirable side effects, such as loss of hair from the head and body, affecting patients who undergo chemotherapy.

Radiotherapy also has unwanted effects. In fact, like chemotherapy, it considerably weakens the body and even the healthy organs of the patient are subject to its direct effects, even if only partially.

Therefore, in both cases, it is important to be able to minimize their application so as to prevent the side effects from being too great.

Specifically, IORT (Intra-Operative Radio Therapy) consists of irradiating the tumour bed or residual tumour during surgery; that technique allows minimization of the dose delivered to healthy tissue and therefore maximization of the dose delivered to the target, thanks to the possibility of inserting dedicated screens in the surgical opening or the possibility of mobilizing the healthy tissue and/or organs at risk.

IORT has become established in recent years thanks to the development of mobile accelerators, designed to carry out treatment directly in the operating room. One of the crucial aspects of an accelerator for IORT is the quantity of scatter radiation produced during the treatment in the operating room.

The radiation protection of an IORT accelerator defines the limits of use and, therefore, together with the dimensions and the weight of the system, is the key element which makes the investment sound.

In fact, the maximum number of treatments which can be carried out in a predetermined time interval is limited by the quantity of scatter radiation to which operators and the public are exposed.

International guidelines, adopted at national level, taken from the document "*Structural Shielding Design and Evaluation for Megavoltage X- and Gamma Rays for Radiotherapy Facilities*", NCRP REPORT 151, 2007, set at 1 mSv/year the maximum dose of scatter radiation to which the population can be exposed; this limit is also stated as 20 μSv/week.

Therefore, the parameter which identifies the effectiveness of an accelerator in terms of radiation protection is the ratio of scatter radiation measured at a predetermined distance to the quantity of dose delivered on the target; the lower this parameter is, measured in μSv/Gy, the higher the deliverable dose quantity is and therefore the higher the number of treatments which can be carried out is.

However, in the case of an accelerator dedicated to intra-operative radiotherapy which operates in a standard operating room, it is necessary to consider the scatter radiation in the entire surrounding space (dividable into the regions identified as 1, 2 and 3 in the accompanying FIG. 1, which respectively correspond to an upper plane, an installation plane and a lower plane) and therefore the maximum scatter radiation value must be identified (commonly identified as the "hot spot"; the value of this hot spot determines the maximum dose quantity deliverable in the time interval identified.

For example, if the hot spot provides the value 0.2 µSv/Gy in the lower plane 3, with the maximum radiation value in a week being set at 20 µSv/week, then the maximum dose quantity deliverable is given by 20 µSv/week divided by 0.2 µSv/Gy, that is to say 100 Gy/week.

The weekly workload is given by the minimum value of the workloads at the different points.

Taking all of that into account, the traditional design strategies and construction techniques do not currently allow the production of a dedicated accelerator, with a weight below 600 kg, which has minimal scatter radiation values suitable for establishing conditions which allow more than 5 treatments per week to be carried out in the above-mentioned standard operating room.

The general aim of this invention is, therefore, to overcome the above-mentioned disadvantages of the prior art and, in particular, to provide a device for radiotherapy treatment of cancer patients which allows a reduction in the scatter radiation in all of the regions of a standard operating room.

Another aim of this invention is to provide a device for radiotherapy treatment of cancer patients which allows the minimization of scatter radiation both in the patient plane and in the planes below and above, keeping the dimensions and weights absolutely compatible with those of a traditional type of device operating in a standard operating room.

These and other aims are achieved by a device for radiotherapy treatment of cancer patients, according to the appended claim 1.

Other technical characteristics of the device for radiotherapy treatment according to the invention are set out in the other dependent claims.

Advantageously, this invention proposes, starting with identification of the problem, a highly innovative solution, which allows the minimization of scatter radiation in the entire space surrounding the device, inside a standard operating room, while keeping the dimensions and weights of the device compatible with those of a traditional type of machine.

Other structural and functional features of this invention and the related advantages over the prior art are more apparent from the following description, with reference to an example and preferred non-limiting embodiment of the device for radiotherapy treatment of cancer patients according to this invention, illustrated in the accompanying drawings, in which.

Figure 1:
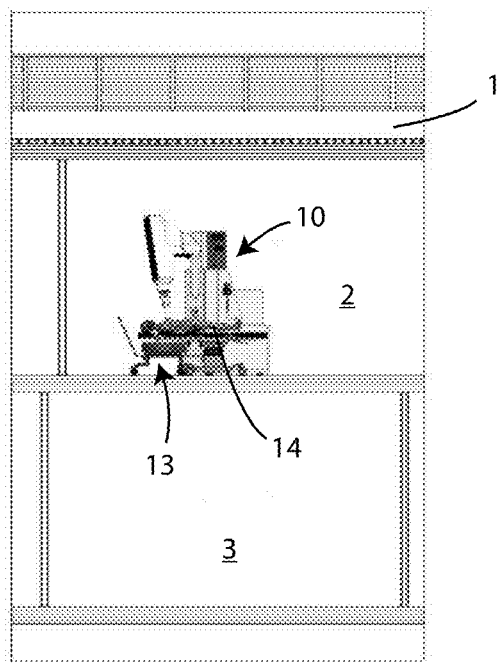
FIG. 1 is a schematic view of a standard operating room, divided into a region for installation of the device for radiotherapy treatment according to this invention, as well as a region above and a region below.

With reference to the accompanying figures, the radiation generated by the IORT device for radiotherapy treatment 10 and scattered in the regions 1, 2 and 3 of a standard operating room can, according to known publications (such as the document "*Structural Shielding Design and Evaluation for Megavoltage X- and Gamma Rays for Radiotherapy Facilities*", NCRP REPORT 151, 2007), be traced back to five different sources:

1) primary beam scatter, even though this component is not present in the case of IORT radiotherapy devices, because the beam is collimated directly and entirely on the target to be treated, which fully absorbs it;

2) leakage radiation (LR), that is to say, the leakage radiation from the accelerator 11 of the radiotherapy device 10;

3) patient 14 scatter radiation (PSR);

4) wall scatter radiation (WSR), which, in general, at any point may be expressed as a sum of the leakage radiation (LR) and the patient scatter radiation (PSR), such that WSR is a linear combination of LR and PSR with coefficients to be determined point by point (WSR=axLR+bxPSR);

5) secondary radiation, which is a completely negligible component.

Figure 2:
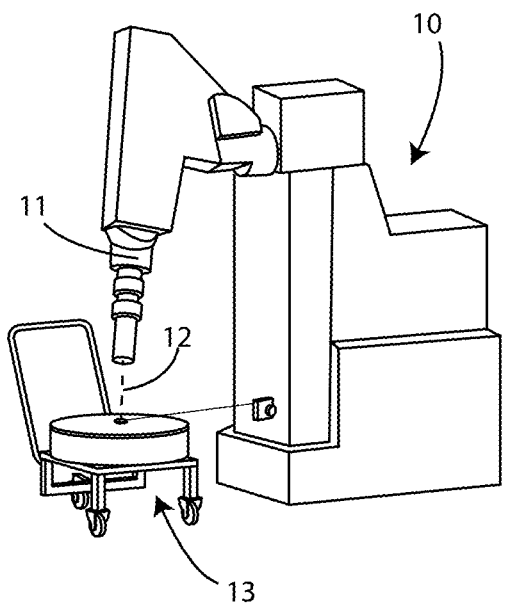
FIG. 2 is a schematic side view of the device for radiotherapy treatment of cancer patients, according to the invention.
Figure 3:
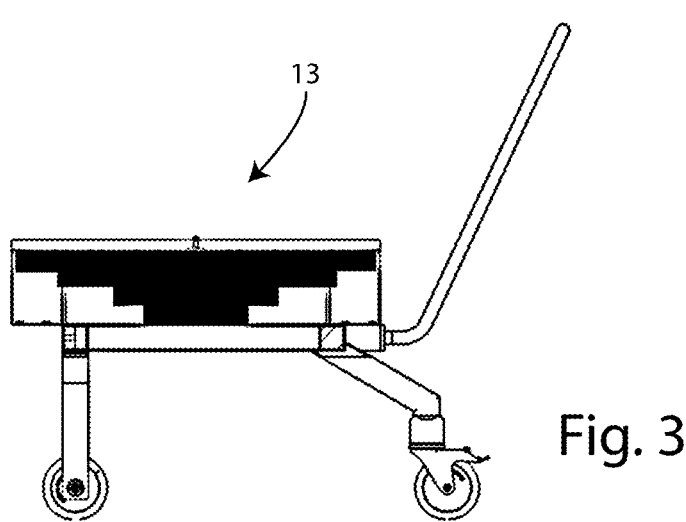
FIG. 3 shows the geometry of a screen used in the device for radiotherapy treatment, according to this invention.

One of the main terms is the patient 14 scatter radiation (PSR), that is to say, the photons generated on the target (patient 14) by the beam of electrons 12 exiting the accelerator 11 of the IORT device 10, through the Bremsstrahlung process; that radiation has a cardioid distribution, extremely intense along the direction of the electron beam 12 and requires specific shielding, since it cannot be limited in any way, but only shielded. That specific shielding, in itself known, which is the ideal compromise between effectiveness and weight, has a pyramid structure, such as that labelled 13 in the accompanying FIGS. 1, 2 and 3.

Therefore, as already described, it is evident that, in order to reduce the total scatter radiation in the various regions 1, 2, 3 of a standard operating room, it is necessary to minimize the leakage radiation (LR) from the accelerator 11 of the IORT radiotherapy device 10.

Figure 4:
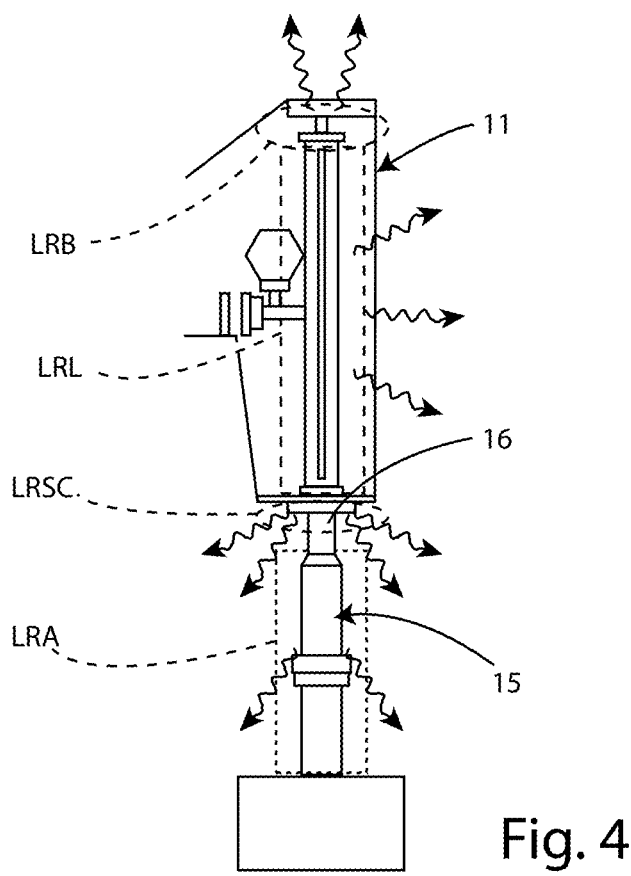
FIG. 4 is a schematic view of the various components of the leakage radiation from the device for radiotherapy treatment.

In the case of an accelerator 11 of an IORT radiotherapy device 10, the leakage radiation LR is the sum of four independent terms (as shown in detail in the accompanying FIG. 4):

the so-called backward radiation LRB, caused by scattering of electrons on the accelerating structure 11 when the oscillating electric field is inverted;

the leakage radiation LRL from the accelerating structure 11, caused by scattering between the electron beam 12 and the accelerating structure itself (this phenomenon occurs if the electron beam radial dynamics are not adequately controlled);

the leakage radiation LRSC caused by the impact of the electron beam 12 on the scattering filter 16 of the accelerator 11 (however, the presence of the scattering filter 16 is made necessary by the need to keep the SSD (distance between the source and the surface of the target) within a range compatible with use in a standard operating room (that is to say, typically, within 70 cm) and to supply a maximum energy of 12 MeV, so as to allow adequate treatment of the target in the IORT technique (with a maximum dose variation within 10% on a target approximately 3.5 cm thick);

the leakage radiation LRA, caused by scattering between the electron beam 12 and the applicator 15.

Limitation of the radiations LRB, LRL and LRA may be effectively dealt with in various ways and using known techniques, whilst until now there has not been any system available which is capable of managing the radiation LRSC produced by the scattering filter 16. This invention solves this aspect, providing a technical solution capable of minimizing that quantity.

As already indicated, the leakage radiation LRSC produced by the scattering filter 16 is an ineliminable factor and must be suitably shielded.

The solution is to design an optical system for collimating the electron beam 12 which maximizes the transmission of electrons and which at the same time is able to shield the photons produced by the scattering filter 16; all of that considering the fact that the maximum energy of the photons produced along the direction of the beam 12 is equal to the energy of the electrons, whilst the maximum energy of the photons produced in the plane perpendicular to the direction of the beam 12 is approximately one quarter (by way of example, in the case of an electron beam 12 with energy equal to 12 MeV, the thickness TVL (shielding thickness which reduces the intensity of the X rays to one tenth) along the axis is 5 cm, whilst in the plane perpendicular to it is 1.3 cm).

Figure 5:
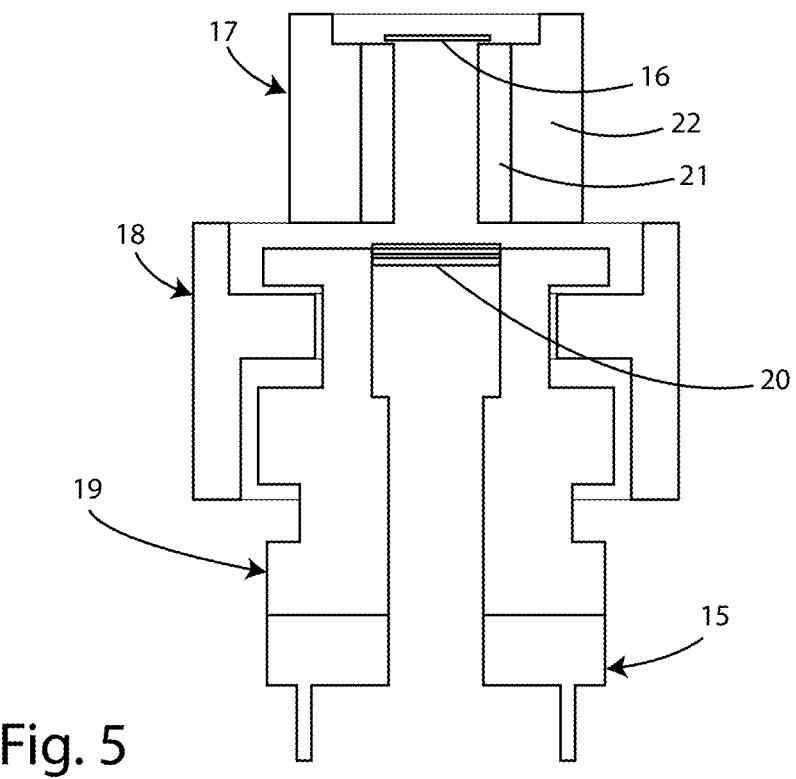
FIG. 5 is a partial cross-section of the device for radiotherapy treatment according to the invention, illustrating the shielding systems adopted.

The collimating system made according to this invention is shown in detail in the accompanying FIG. 5 and has:

a scattering filter 16, which is preferably made of metal material with a low atomic number (Z) and with a thickness of between 0.5 and 0.8 mm;

a primary screen 17, configured to shield the radiation produced by the scattering filter 16;

a secondary screen 18, configured to shield the photons produced on the primary screen 17, entirely made of material suitable for shielding photons (such as Lead and Tungsten) and configured to intercept the entire lobe produced on the primary, in such a way as to suitably limit the photons produced both on the patient plane and on the lower plane;

a collimating apparatus 19, made of material with a low atomic number (Z) and highly resistant to damage from ionizing radiations (such as Tecapeek), which provides for housing the monitor chambers 20.

Specifically, the primary screen 17 has an internal cylinder 21 made of a material with a low atomic number (Z) and with a thickness such as to reduce the energy of the electrons incident on the outer cylinder by at least a factor of 3; by way of example, considering 12 MeV as the maximum energy of the electrons and PTFE as the material of the internal cylinder 21, then the maximum energy incident on the walls of the cylinder 21 is approximately 7 MeV, whilst the thickness of the PTFE is determined, to a first approximation (CSDA), using Harder's equation, $E_{TH}/E_0 = 1 - TH/R_p$ (where $R_p$ is the practical range and TH the thickness of the cylinder 21 made of PTFE), which give the solution TH≥1.44 cm.

Moreover, the primary screen 17 also has an outer cylinder 22, made of a material suitable for shielding photons (such as Lead or Tungsten) and having a total thickness equal to at least 2 TVL for the 90° beam, that is to say, in the example examined, at least 2.6 cm if using Lead or 2 cm if using Tungsten.

Specifically, the secondary screen 18 has a series of passage holes with diameters such as to allow both an optimum flow of the electron beam 12 and an adequate shielding of the photons produced by the scattering filter 16 and by the end portion of the primary screen 17.

Moreover, the thickness of the secondary screen 18 is equal to at least 1 TVL for the 90° beam, that is to say, in the example examined, 1.3 cm if using Lead or 1 cm if using Tungsten.

From the description, the characteristics of the device for radiotherapy treatment of cancer patients, which is the object of this invention, clearly emerge, as do the advantages thereof.

Lastly, it is clear that the device in question may be modified and adapted in several ways without thereby departing from the principles of novelty of the inventive concept as claimed in the appended claims, while it is clear that in the practical actuation of the invention, the materials, the shapes and the dimensions of the illustrated details can be of any type according to requirements, and can be replaced by other technically equivalent elements.

What is claimed is:

1. An IORT device (10) for radiotherapy treatment of cancer patients, comprising:
a source of particles, an accelerating device (11) which sends a beam of particles (12) on a target (14) through an applicator (15), a scattering filter (16) which allows to maintain the distance between said source of particles and said target (14) within a range compatible with the use of said IORT device (10) in standard operating rooms and which allows to provide a maximum energy of 12 MeV, so as to allow a suitable treatment of the target (14), and an optical system for collimating said beam of particles (12) which is placed between said scattering filter (16) and said applicator (15), characterized in that said optical collimating system of said beam of particles (12) comprises a primary screen (17), configured to shield the radiation produced by said scattering filter (16), a secondary screen (18) configured to shield the photons produced on said primary screen (17), and a collimating apparatus (19), which provides for housing the monitor chambers (20).

2. The IORT device (10) according to claim 1, characterized in that said scattering filter (16) is made of a metal material with a low atomic number (Z).

3. The IORT device (10) according to claim 1, characterized in that said scattering filter (16) has a thickness ranging from 0.5 to 0.8 mm.

4. The IORT device (10) according to claim 1, characterized in that said secondary screen (18) is entirely made of material suitable for shielding photons, such as Lead and Tungsten, and is configured to reduce the photons produced both on the target plane (14) and on the lower plane.

5. The IORT device (10) according to claim 1, characterized in that said collimating apparatus (19) is made of a material with a low atomic number (Z) and highly resistant to damage from ionizing radiations, such as the Tecapeek.

6. The IORT device (10) according to claim 1, characterized in that said primary screen (17) has an outer cylinder (22), made of a material suitable for shielding photons, such as Lead or Tungsten, and having a total thickness equal to at least 2 TVL for the 90° beam, and an internal cylinder (21), made of a material with a low atomic number (Z) and having a thickness such as to reduce the energy of the particles incident on said outer cylinder (22) of at least a 3 factor.

7. The IORT device (10) according to claim 1, characterized in that said secondary screen (18) has a series of passage holes with diameters such as to allow an adequate flow of said particle beam (12) and a shielding of the photons produced by said scattering filter (16) and by an end portion of said primary screen (17).

8. The IORT device (10) according to claim 1, characterized in that said secondary screen (18) has a thickness equal to at least 1 TVL for the 90° beam.

* * * * *